United States Patent
Turowski-Wanke et al.

(10) Patent No.: US 6,541,016 B1
(45) Date of Patent: *Apr. 1, 2003

(54) MIXTURES OF ALKYLPHOSPHORIC ESTERS AND USE THEREOF AS COSMETIC AND PHARMACEUTICAL EMULSIFIERS

(75) Inventors: Angelika Turowski-Wanke, Kelkheim (DE); Matthias Löffler, Niedernhausen (DE); Oliver Eyrisch, Essen (DE); Werner Skrypzak, Hofheim/Lorsbach (DE)

(73) Assignee: Clariant GmbH, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/031,430

(22) Filed: Feb. 26, 1998

(30) Foreign Application Priority Data

Feb. 27, 1997 (DE) .......................................... 197 07 800

(51) Int. Cl.⁷ .............................. A61K 7/00; B01F 3/08; B01F 17/00; C07D 277/04
(52) U.S. Cl. ........................ 424/401; 516/56; 516/199; 548/180; 548/182
(58) Field of Search .......................... 424/401; 558/180, 558/182; 516/56, 199

(56) References Cited

U.S. PATENT DOCUMENTS

| 4,101,457 A | 7/1978 | Place et al. ................. 252/559 |
| 4,152,421 A | 5/1979 | Tsutsumi et al. ............. 424/57 |
| 4,247,424 A | 1/1981 | Kuzel et al. ................. 252/528 |
| 4,704,165 A | * 11/1987 | Nakamura ................... 106/308 |
| 5,565,601 A | * 10/1996 | Ihara ........................... 558/102 |
| 6,066,753 A | * 5/2000 | Turowski-Wanke et al. ..... 558/208 |

FOREIGN PATENT DOCUMENTS

| DE | 2024051 | 12/1971 |
| DE | 2744980 | 4/1978 |
| EP | 0201040 | 11/1986 |
| EP | 0227012 | 7/1987 |
| EP | 0265702 | 5/1988 |
| EP | 0347844 | 12/1989 |
| EP | 0442701 | 8/1991 |
| EP | 0553241 | 4/1995 |
| GB | 2139112 | 11/1984 |
| WO | WO 92/07543 | 5/1992 |

OTHER PUBLICATIONS

CA Abstract, AN: 1967:40679, Lukesch et al., 1967.*
CA Abstract, AN: 1976:126641, Cajkovac et al., 1976.*
PCT International Search Report.
Derwent Patent Family Report and/or Abstract.

* cited by examiner

Primary Examiner—Russell Travers
Assistant Examiner—Shengjun Wang
(74) Attorney, Agent, or Firm—Susan S. Jackson; Scott E. Hanf

(57) ABSTRACT

This invention relates to monoalkyl phosphoric esters, dialkyl phosphoric esters, and, in small amounts, trialkyl phosphoric esters or salts thereof, which are preferably based on β-branched fatty alcohols, particularly Guerbet alcohol, which are effective in lowering the surface tension of both polar and also nonpolar liquids, and which have high stability, even at elevated temperatures, and low sensitivity to electrolytes and acids. The invention further relates to the use of such mixtures as emulsifiers in cosmetic and pharmaceutical formulations, and to the resulting products.

6 Claims, No Drawings

MIXTURES OF ALKYLPHOSPHORIC ESTERS AND USE THEREOF AS COSMETIC AND PHARMACEUTICAL EMULSIFIERS

This application claims the foreign priority of FED REP GERMANY application 197 07800-1, filed Feb. 27, 1997

This invention relates to mono-, di- and, in small amounts, also trialkylphosphoric esters or salts thereof, which are preferably based on β-branched fatty alcohols, particularly preferably on Guerbet alcohol, and which are very effective in lowering the surface tension of both polar and also nonpolar liquids, and have high stability, even at elevated temperatures, and low sensitivity to electrolytes and acids.

The invention further relates to the use of such mixtures as emulsifiers in cosmetic and pharmaceutical formulations, and also to the resulting products.

The use of emulsifiers in the preparation of creams, lotions, ointments etc., which comprise two or more immiscible substances (e.g. water, oil, organic and inorganic constituents), has been known for some time. The emulsifiers used are surfactants, e.g. soaps of alkali metals and alkanolamines, mono- and diglyceryl esters of fatty acids, but also certain naturally occurring substances (e.g. lecithins and waxes) and inorganic substances (e.g. bentonites).

EP-B-0 553 241 discloses the use of mixtures of alkyloligoglucosides, fatty alcohols and, if desired, polyglucose for the preparation of emulsions. WO-92/07543 discloses the use of alkyloligoglucosides with fatty alcohols and partial glycerides as cosmetic emulsifiers.

EP-B-0 201 040 describes the emulsifying power of metal salts of dialkyl phosphates, and EP-B-0 227 012 describes that of monophosphoric esters.

GB-A-2 139 112 discloses an emulsifier mixture of mono- and diesters of phosphoric acid, some of which are also ethoxylated, in a ratio of from 100:0 to 70:30 and also a nonionic surfactant.

The use of β-branched monoalkylphosphoric esters as emulsifiers is disclosed in EP-A-0 265 702.

The specified emulsifiers do, however, also have unfavorable properties, such as low stability at elevated temperatures, limited miscibility with or solubility in aqueous or organic media and they reduce the emulsifying power on addition of salt-like components.

The object was thus to develop high-performance stable emulsifiers which are insensitive to salt-like components, for example electrolytes. For applicational reasons, they should be liquid at room temperature and, to ensure good tolerability by theskin, have a pH of from about 5 to 7.

Surprisingly, it has been found that mixtures of mono-, di- and trialkylmonophosphoric esters have the required properties.

The invention relates to mixtures of mono-, di- and trialkylmonophosphoric esters of the formulae I, II and III $$R-O-\underset{\underset{O}{\|}}{P}-OY \quad (I)$$
$$\overset{|}{OX}$$

$$R^1-O-\underset{\underset{O}{\|}}{P}-OX \quad (II)$$
$$\overset{|}{\underset{O}{R^2}}$$

$$R^1-O-\underset{\underset{O}{|}}{P}=O \quad (III)$$
$$\overset{|}{\underset{R^3}{O}}\overset{|}{\underset{}{}}$$
$$\overset{|}{\underset{}{R^2}}$$

in which
R, $R^1$, $R^2$ and $R^3$, which may be identical or different, are straight-chain or branched alkyl groups having from 8 to 36 carbon atoms, and
X and Y, which may be identical or different, are hydrogen, alkali metal or alkaline earth metal, substituted or unsubstituted ammonium or basic organic groups.

Basic organic groups under the meaning of X and Y are, for example, basic amino acids, such as arginine, ornithine and lysine, and also alkanolamines, e.g. triethanolamine or monoethanolamine. Examples for substituted ammonium include $C_8$–$C_{22}$-alkylammonium.

The invention further relates to the use of these mixtures of alkylphosphoric esters as emulsifiers in cosmetic or pharmaceutical formulations and also to cosmetic or pharmaceutical formulations which comprise these esters.

The mixtures according to the invention comprise the monoesters of the formula I and also the diesters of the formula II, in each case in amounts of from about 30 to 60% by weight, in particular from about 40 to 50% by weight. The triesters of the formula III are present in the mixtures according to the invention in amounts of between about 0.5 and 5% by weight, preferably about 1 to 2% by weight.

The phosphoric ester mixture is normally used in amounts of from 0.1 to 5 percent by weight, preferably in amounts of from 0.3 to 3 percent by weight, based on finished formulations.

It has been found that mixtures of phosphoric esters, comprising mono-, di- and triesters of the formulae I, II and III, have excellent emulsifier properties when R, $R^1$, $R^2$ and $R^3$ are β-branched alkyl groups having from 16 to 20 carbon atoms. The parent alcohols of these radicals are referred to as Guerbet alcohols. Alkylphosphoric esters in which R, $R^1$, $R^2$ and $R^3$ are β-branched alkyl groups having from 16 to 20 carbon atoms are a preferred embodiment of this invention.

The alkylphosphoric esters are synthesized by reacting tetraphosphorus decaoxide and alkyl fatty alcohols to form mono- and diesters in an approximate molar ratio of 1:1, with small amounts of triester, as shown in the reaction equation (R is used here for all the R, $R^1$, $R^2$ and $R^3$ radicals):

$$P_4O_{10} + 6\,R-OH \longrightarrow 2\,O=\underset{\underset{O-R}{|}}{\overset{\overset{O-H}{|}}{P}}-OH +$$

$$2\,O=\underset{\underset{O-R}{|}}{\overset{\overset{O-H}{|}}{P}}-R + O=\underset{\underset{O-R}{|}}{\overset{\overset{O-R}{|}}{P}}-O-R.$$

The alkylphosphoric ester mixtures are yellowish to white, in some cases solid or waxy, or viscous, liquid substances having melting points of between −5° C. and 80° C. and iodine color numbers of from <4 to <0.5.

$P_4O_{10}$ reacts with $C_{16}/C_{20}$-Guerbet alcohol to give a phosphoric ester mixture in which R, $R^1$, $R^2$ and $R^3$ = $C_{16}$–$C_{20}$-β-branched alkyl which has particularly advantageous physicochemical characteristics. The pale yellow, liquid mixture, comprising about 40–60% by weight of the monoester, about 30–50% by weight of the diester and up to 10% by weight of the triester, has a melting point of <−5° C., an iodine color number of <1.0 and has good solubility both in polar and also in nonpolar organic substances, such as paraffin, soybean oil and isopropyl palmitate.

The phosphoric ester mixtures according to the invention, preferably those in which R, $R^1$, $R^2$ and $R^3$ are β-branched $C_{16}$–$C_{20}$-alkyl, are suitable, in particular, for the preparation of oil-in-water emulsions, but also for water-in-oil emulsions preferably for the preparation of alcohol-free emulsions.

The performance of an emulsifier is correlated with the reduction in surface tension. Phosphoric esters having the composition described above are notable for their surface tension-lowering effect. Surprisingly, it has been found that phosphoric esters based on Guerbet alcohols drastically reduce the surface tension which the performance as an emulsifier reflects.

TABLE 1

The effect of a variety of phosphoric esters on the surface tension of oils of varying polarity

| Phosphoric ester | Paraffin oil | Cetearyl isononanoate | Soybean oil |
| --- | --- | --- | --- |
| Lauryl | 28 | 16.5 | 16 |
| Stearyl | 16 | 15.8 | 15.5 |
| Isostearyl | 11 | 8.5 | 9.0 |
| Isooctadecyl | 1.5 | 2.5 | 3.0 |
| Oleyl | 13 | 11 | 9.0 |
| Behenyl | 36 | 24 | 17.5 |

Surface tension in mN/m
Temperature 25° C., concentration 1.5 g of phosphoric ester in 1 liter of water, pH 7, Na salt
"Cetearyl" refers to a mixture of cetyl and stearyl.

The surface tension was determined using a Lauda drop volume tensiometer.

The term "phosphoric ester" in this table means a novel mixture of approximately equal parts of mono- and diesters and also a small amount of triesters.

Stability tests with a variety of oils, such as squalene, soybean oil, cetearyl isononanoate and isopropyl palmitate, showed that emulsions which comprise the phosphoric esters based on Guerbet alcohols show no cracking whatsoever in the 30-day storage test at 40, 45 and 50° C. Comparable results were obtained in the centrifuge test at different emulsifier concentrations.

The emulsifiers according to the invention are notable for being very effective in lowering the surface tension, even at elevated temperatures, of polar and nonpolar constituents. The emulsifiers, some of which are liquid, have improved stability to electrolyte additives and acids and a long shelf life. They have a pH in the range from 5 to 7 and can thus be used as emulsifiers which are very kind to the skin, preferably in skincare products.

The nonaqueous part of the emulsions, which largely comprises the emulsifier and oily substances and usually corresponds to the solids content, is usually from 5 to 95% by weight and preferably from 15 to 75% by weight. This means that the emulsions may contain from 5 to 95% by weight, and preferably from 25 to 85% by weight, of water, depending on whether the intention is to prepare lotions having a comparatively low viscosity, or creams and ointments having a high viscosity.

Examples of suitable oily substances are Guerbet alcohols based on fatty alcohols having from 6 to 18, preferably from 8 to 10, carbon atoms, esters of linear $C_6$–$C_{13}$-fatty acids with linear $C_6$–$C_{20}$-fatty alcohols, esters of branched $C_6$–$C_{13}$-carboxylic acids with linear $C_6$–$C_{20}$-fatty alcohols, esters of linear $C_6$–$C_{18}$-fatty acids with branched alcohols, in particular 2-ethylhexanol, esters of linear and/or branched fatty acids with polyvalent alcohols (such as, for example, dimerdiol or trimerdiol) and/or Guerbet alcohols, triglycerides based on $C_6$–$C_{10}$-fatty acids, vegetable oils, branched primary alcohols, substituted cyclohexanes, Guerbet carbonates, dialkyl ethers and/or aliphatic or aromatic hydrocarbons. The proportion of oily substances in the nonaqueous part of the emulsions can be from 5 to 95% by weight and, preferably, from 15 to 75% by weight.

The emulsions can be used as skincare products, such as, for example, day creams, night creams, beauty creams, nourishing creams, body lotions, ointments and the like, and may comprise further auxiliaries and additives, such as coemulsifiers, superfatting agents, fats, waxes, stabilizers, biogenic active substances, glycerin, preservatives, dyes and perfumes.

It is essential to the invention that the described mixtures of phosphoric esters can also be used without co-use of a nonionic surfactant as coemulsifier. The co-use of coemulsifiers is thus not imperative, but possible.

Suitable nonionogenic O/W coemulsifiers include the products of the addition reaction of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group; $C_{12}$–$C_{18}$-fatty acid mono- and diesters of the products of the addition reaction of from 1 to 30 mol of ethylene oxide with glycerin; glyceryl mono- and diesters and sorbitan mono- and diesters of saturated and unsaturated fatty acids having from 6 to 22 carbon atoms and the products of their addition reaction with ethylene oxide; products of the addition reaction of from 15 to 60 mol of ethylene oxide with castor and/or hydrogenated castor oil; polyol and, in particular, polyglyceryl esters, such as, for example, polyglyceryl polyricinoleate and polyglyceryl poly-12-hydroxystearate. Mixtures of compounds from one or more of these classes of substance are also suitable. The products of the addition reaction of ethylene oxide and/or propylene oxide with fatty alcohols, fatty acids, alkylphenols, glyceryl mono- and diesters and also sorbitan mono- and diesters of fatty acids, or with castor oil are known products which are available commercially. They are homolog mixtures whose average degree of alkoxylation corresponds to the ratio of the amounts of ethylene oxide and/or propylene oxide and substrate used in the addition reaction. $C_{12}$–$C_{18}$-fatty acid mono- and diesters of products of the addition reaction of ethylene oxide with glycerin are known from DE-20 24 051 as superfatting agents for cosmetic preparations.

Superfatting agents which can be used are substances such as, for example, polyethoxylated lanolin derivatives, lecithin derivatives, polyol fatty acid esters, monoglycerides and fatty acid alkanolamides, the latter also being used as foam stabilizers. Typical examples of fats are glycerides, and suitable waxes are, inter alia, beeswax, paraffin wax or microwaxes, if desired in combination with hydrophilic waxes, e.g. cetyl stearyl alcohols. Stabilizers which may be used are metal salts of fatty acids, such as, for example, magnesium stearate, aluminum stearate and/or zinc stearate.

Biogenic active substances are taken to mean, for example, plant extracts and vitamin complexes. Examples of suitable preservatives are phenoxyethanol, formaldehyde solution, parabens, pentanediol and sorbic acid. Examples of suitable pearlizing agents are glycol distearic esters, such as ethylene glycol distearate, but also fatty acid monoglycol esters. The dyes which can be used are the substances which are approved and suitable for cosmetic purposes, such as are listed, for example, in the publication "Kosmetische Farbemittel" [Cosmetic Colorants] from the Farbstoffkommission der Deutschen Forschungsgemeins chaft [Dyes Commission of the German Research Society], Verlag Chemie, Weinheim, 1984, p. 81–106.

The total amount of auxiliaries and additives can be from 1 to 10% by weight, preferably from 2 to 5% by weight, based on the product.

The products can be prepared in a manner known per se, i.e. for example by hot, hot-hot/cold or PIT emulsification.

EXAMPLES

O/W Skin milk
"Ethylene oxide-free", can be prepared cold

| | Composition | |
|---|---|---|
| A | ®HOSTAPHAT VCG 120 (Hoechst AG) | 1.50% |
| | Paraffin oil, low-viscosity | 5.00% |
| | ®MIGLYOL 812 (Dynamit Nobel) | 4.00% |
| | Isopropyl palmitate | 6.00% |
| | Jojoba oil | 2.00% |
| | Soybean oil | 3.00% |
| B | ®CARBOPOL 980 (Goodrich) | 0.50% |
| C | ®AQUAMOLLIN BC Powder, high-conc. (Hoechst AG) | 0.10% |
| | Citric acid (10%) | 0.30% |
| | NaOH (10%) | 3.20% |
| | Glycerin | 3.00% |
| | Water | 71.0% |
| | Preservative | q.s. |
| D | Paraffin oil | 0.30% |

| | Preparation |
|---|---|
| I | Add B to A, then stir in C and mix well |
| II | Stir D into I |
| III | Finally, homogenize the emulsion |

O/W Cream
"Ethylene oxide-free", mineral oil-free

| | Composition | |
|---|---|---|
| A | ®HOSTAPHAT VCG 120 (Hoechst AG) | 1.00% |
| | ®HOSTACERIN DGMS (Hoechst AG) | 2.50% |
| | ®MIGLYOL 812 (Dynamit Nobel) | 3.00% |
| | ®CETIOL SN (Henkel KGaA) | 4.00% |
| | Isopropyl palmitate | 5.00% |
| | Wheat germ oil | 1.00% |
| | Jojoba oil | 3.00% |
| | Soybean oil | 4.00% |
| B | ®CARBOPOL 980 (Goodrich) | 0.60% |
| C | ®HOSTAPON KCG (Hoechst AG) | 0.60% |
| | ®AQUAMOLLIN BC Powder, high-conc. (Hoechst AG) | 0.10% |
| | Citric acid (10%) | 0.30% |
| | NaOH (10%) | 2.90% |
| | Glycerin | 3.00% |
| | Water | 68.60% |
| | Preservative | q.s. |
| D | Perfume oil | 0.40% |

| | Preparation |
|---|---|
| I | Melt A at about 80° C., then add B |
| II | Heat C to about 80° C. |
| III | Add I to II with stirring and stir while cold |
| IV | Stir in III at about 35° C. |
| V | Finally, homogenize the emulsion |

O/W Skin milk
"Ethylene oxide-free"; can be prepared cold

| | Composition | |
|---|---|---|
| A | ®HOSTAPHAT VCG 120 (Hoechst AG) | 1.50% |
| | Isopropyl palmitate | 6.00% |
| | Parrafin oil, low-viscosity | 5.00% |
| | ®MIGLYOL 812 (Dynamit Nobel) | 4.00% |
| | Soybean oil | 3.00% |
| | Jojoba oil | 2.00% |
| B | ®CARBOPOL 980 (Goodrich) | 0.50% |
| C | ®AQUAMOLLIN BC Powder, high-conc. (Hoechst AG) | 0.10% |
| | Citric acid (10%) | 0.30% |
| | Glycerin | 3.00% |
| | Water | 71.10% |
| | Sodium hydroxide (10%) | 3.20% |
| | Preservative | q.s. |
| D | Perfume oil | 0.30% |

| | Preparation |
|---|---|
| I | Add B to A, then stir in C and mix well |
| II | Stir D into I |
| III | Finally, homogenize the emulsion. |

O/W Cream
Ethylene oxide-free

| | Composition | |
|---|---|---|
| A | ®HOSTAPHAT VCG 120 (Hoechst AG) | 1.00% |
| | ®HOSTACERIN DGMS (Hoechst AG) | 2.50% |
| | Isopropyl palmitate | 6.00% |
| | Paraffin oil, low-viscosity | 5.00% |
| | ®MIGLYOL 812 (Dynamit Nobel) | 4.00% |
| | Soybean oil | 3.00% |
| | Jojoba oil | 2.00% |
| B | ®CARBOPOL 980 (Goodrich) | 0.60% |
| C | ®AQUAMOLLIN BC Powder, high-conc. (Hoechst AG) | 0.10% |
| | Citric acid (10%) | 0.30% |
| | Glycerin | 3.00% |
| | Water | 68.90% |
| | Sodium hydroxide (10%) | 3.20 |
| | Preservative | q.s. |
| D | Perfume oil | 0.40% |

| | Preparation |
|---|---|
| I | Melt A at about 60° C., then add B |
| II | Heat C to about 60° C. |
| III | Add I to II with stirring and stir while cold |
| IV | Stir in III at about 35° C. |
| V | Finally, homogenize the emulsion |

O/W Skin milk
Ethylene oxide-free, mineral oil-free

| | Composition | |
|---|---|---|
| A | ®HOSTAPHAT VCG 120 (Hoechst AG) | 1.00% |
| | ®HOSTACERIN DGMS (Hoechst AG) | 1.50% |
| | Isopropyl palmitate | 5.00% |
| | ®CETIOL SN (Henkel KGaA) | 4.00% |
| | Soybean oil | 4.00% |
| | ®MIGLYOL 812 (Dynamit Nobel) | 3.00% |
| | Jojoba oil | 3.00% |
| | Wheat flour | 1.00% |
| B | ®CARBOPOL 980 (Goodrich) | 0.60% |

-continued

| | | |
|---|---|---|
| C | ®AQUAMOLLIN BC Powder, high-conc. (Hoechst AG) | 0.10% |
| | Citric acid (10%) | 0.30% |
| | Glycerin | 3.00% |
| | Water | 71.00% |
| | Sodium hydroxide (10%) | 2.40% |
| | Preservative | q.s. |
| D | Perfume oil | 0.30% |

| Preparation | | |
|---|---|---|
| I | Melt A at about 60° C., then add B | |
| II | Heat C to about 60° C. | |
| III | Add I to II with stirring and stir while cold | |
| IV | Stir in III at about 35° C. | |
| V | Finally, homogenize the emulsion | |

O/W Skin milk
Ethylene oxide-free

| Composition | | |
|---|---|---|
| A | ®HOSTAPHAT VCG 120 (Hoechst AG) | 1.00% |
| | ®HOSTACERIN DGMS (Hoechst AG) | 2.00% |
| | Isopropyl palmitate | 6.00% |
| | Paraffin oil, low-viscosity | 5.00% |
| | ®MIGLYOL 812 (Dynamit Nobel) | 4.00% |
| | Soybean oil | 3.00% |
| | Jojoba oil | 2.00% |
| B | ®CARBOPOL 980 (Goodrich) | 0.40% |
| C | ®AQUAMOLLIN BC Powder high-conc. (Hoechst AG) | 0.10% |
| | Ethylenediaminetetraacetic acid, sodium salt | |
| | Citric acid (10%) | 0.30% |
| | Glycerin | 3.00% |
| | Water | 71.00% |
| | Sodium hydroxide (10%) | 2.40% |
| | Preservative | q.s. |
| D | Perfume oil | 0.30% |

| Preparation | | |
|---|---|---|
| I | Melt A at about 60° C., then add B | |
| II | Heat C to about 60° C. | |
| III | Add I to II with stirring and stir while cold | |
| IV | Stir in III at about 35° C. | |
| V | Finally homogenize the emulsion | |

O/W Skin milk
can be prepared cold

| Composition | | |
|---|---|---|
| A | ®HOSTAPHAT VCG 120 (Hoechst AG) | 1.50% |
| | ®HOSTACERIN DGI (Hoechst AG) | 2.00% |
| | Paraffin oil, low-viscosity | 8.00% |
| | Isopropyl palmitate | 6.00% |
| | ®CETIOL 868 (Henkel KGaA) | 5.00% |
| B | ®CARBOPOL 980 (Goodrich) | 0.40% |
| C | Water | 75.20% |
| | Sodium hydroxide (10%) | 1.60% |
| | Preservative | q.s. |
| D | Perfume oil | 0.30% |

| Preparation | | |
|---|---|---|
| I | Add B to A, then stir in C | |
| II | Stir D into I | |
| III | Finally, homogenize the emulsion | |

O/W Moisturizing milk

| Composition | | |
|---|---|---|
| A | ®HOSTAPHAT VCG 120 (Hoechst AG) | 1.00% |
| | ®HOSTACERIN DGS (Hoechst AG) | 4.00% |
| | Isopropyl isostearate | 4.00% |
| | ®CETIOL V (Henkel KGaA) | 4.00% |
| | Walnut oil | 4.00% |
| | Paraffin oil, low-viscosity | 3.00% |
| | Antioxidant | q.s. |

-continued

| | | |
|---|---|---|
| B | CARBOPOL 980 (Goodrich) | 0.30% |
| C | ®AQUAMOLLIN BC Powder, high-conc. (Hoechst AG) | 0.10% |
| | Citric acid (10%) | 0.25% |
| | Glycerin | 3.00% |
| | Water | 69.85% |
| | Sodium hydroxide (10%) | 1.20% |
| | Preservative | q.s. |
| D | Perfume oil | 0.30% |

| Preparation | | |
|---|---|---|
| I | Melt A at about 70° C., then add B | |
| II | Heat C to about 70° C. | |
| III | Add I to II with stirring and stir while cold | |
| IV | Stir in III at about 35° C. | |
| V | Finally, homogenize the emulsion | |

The following commercial products were used:

®Carbopol 980

Acrylic acid polymers which have been polymerized in a mixture of ethyl acetate and cyclohexane.

®Miglyol 812

Caprylic triglyceride

®Aquamollin BC Powder, high-conc.

Ethylenediaminetetraacetic acid, sodium salt

®Hostacerin DGMS polyglyceryl-2 stearate

Cetiol SN cetearyl isononanoate

Cetiol 868 isooctyl stearate

®Cetiol V decyl oleate

®hostapon KCG sodium cocoyl glutamate

®hostaphat VCG 120 mono/diphosphoric esters based on $C_{18}$-guerbet alcohol

Hostacerin DGI polyglyceryl-2 sesquiisostearate

What is claimed is:

1. Cosmetic and pharmaceutical emulsion formulations, comprising as emulsifier from 0.1% to 5% by weight of alkyl phosphoric ester emulsifier, said alkyl phosphoric ester emulsifier consists of a mixture of from 30% to 60% by weight of monoalkyl monophosphoric esters, from 30% to 60% by weight of dialkyl monophosphoric esters, and from 0.5% to 5% of trialkyl monophosphoric esters of the formulas I, II and III:

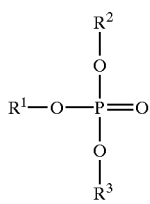

(III)

in which
R, R¹, R² and R³, which may be identical or different, are beta-branched alkyl groups having from 16 to 20 carbon atoms, and X and Y are identical or different, and are selected from the group consisting of hydrogen, alkali metal or alkaline earth metal, substituted or unsubstituted ammonium and basic organic groups.

2. The alkyl phosphoric ester emulsifier mixture as claimed in claim 1, wherein the basic organic groups under the definition of X and Y are basic amino acids selected from the group consisting of arginine, ornithine, lysine, and alkanolamines.

3. The alkyl phosphoric ester emulsifier mixture as claimed in claim 1, which comprises the monoesters of the formula I and the diesters of the formula II in amounts of from 40 to 50% by weight.

4. The alkyl phosphoric ester emulsifier mixture as claimed in claim 1, which comprises the triesters of the formula III in amounts between about 1 and 2 percent by weight.

5. A cosmetic and/or pharmaceutical formulation which comprises the mixture as claimed in claim 1 in amounts from about 0.3 to 3 percent by weight, based on the weight of the formulation.

6. A cosmetic or pharmaceutical emulsion, comprising as emulsifier a mixture of monoalkyl monophosphoric esters, dialkyl monophosphoric esters, and trialkyl monophosphoric esters of the formulas I, II, and III:

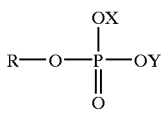

(I)

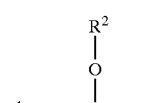

(II)

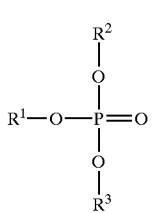

(III)

in which
R, R¹, R² and R³, which may be identical or different, are beta-branched alkyl groups having from 16 to 20 carbon atoms, and X and Y are identical or different, and are selected from the group consisting of hydrogen, alkali metal or alkaline earth metal, substituted or unsubstituted ammonium and basic organic groups, and wherein said mono- and said dialkyl monophosphoric esters are present in said emulsifier mixture at from 30 to 60 weight %.

* * * * *